US005668354A

United States Patent [19]
Falco

[11] Patent Number: 5,668,354
[45] Date of Patent: Sep. 16, 1997

[54] EARPLUG ASSEMBLY AND EYEWEAR ASSEMBLY

[75] Inventor: Robert N. Falco, Indianapolis, Ind.

[73] Assignee: Cabot Safety Intermediate Corporation, Southbridge, Mass.

[21] Appl. No.: 552,213

[22] Filed: Nov. 2, 1995

[51] Int. Cl.⁶ ........................................ A61B 7/02
[52] U.S. Cl. ........................... 181/135; 128/864
[58] Field of Search ........................ 181/129, 130, 181/131, 135; 381/187, 188, 205; 128/864, 867; 455/90

[56] References Cited

U.S. PATENT DOCUMENTS

| | | |
|---|---|---|
| D. 241,881 | 10/1976 | Peterson et al. . |
| D. 245,202 | 7/1977 | Asker . |
| D. 298,356 | 11/1988 | Falco . |
| 2,649,020 | 8/1953 | Wheeler . |
| 2,704,961 | 3/1955 | Weil . |
| 3,667,569 | 6/1972 | Mackey et al. ........... 181/129 |
| 3,871,372 | 3/1975 | Bivins . |
| 4,193,396 | 3/1980 | Wacker .............. 128/864 |
| 4,219,018 | 8/1980 | Draper, Jr. . |
| 4,253,452 | 3/1981 | Powers et al. . |
| 4,314,553 | 2/1982 | Westerdal . |
| 4,353,364 | 10/1982 | Woods . |
| 4,896,679 | 1/1990 | St. Pierre . |
| 4,916,758 | 4/1990 | Jordan-Ross . |
| 4,942,617 | 7/1990 | Boylan ..................... 455/90 |
| 5,074,375 | 12/1991 | Grozil . |
| 5,249,309 | 10/1993 | Berg et al. . |

OTHER PUBLICATIONS

Publication "Ultra low density copolymers for ultra high performance" by Dow Plastics for Packaging Industry Group, Nov. 1992.

*Primary Examiner*—Khanh Dang
*Attorney, Agent, or Firm*—Fishman, Dionne, Cantor & Colburn

[57] ABSTRACT

An earplug assembly. The assembly includes a pair of earplugs adapted for insertion into the ear canal of an individual and an attachment member securely connected to each plug. The attachment member has a first predetermined length and is capable of being extended to a second length. Once extended, the attachment member retains its extended second length.

16 Claims, 2 Drawing Sheets

EARPLUG ASSEMBLY AND EYEWEAR ASSEMBLY

BACKGROUND OF THE INVENTION

1. Field of the Invention.

The present invention relates to hearing protective devices and, more particularly, to an earplug assembly.

2. Description of the Related Art.

Health and safety regulations require that individuals working in noisy environments be protected by wearing appropriate safety equipment, such as hearing protectors. Various types of hearing protectors are currently available to workers for this purpose, such as earplugs, ear muffs and semi-aural hearing protectors. Of these, earplugs have gained universal acceptance in both industrial and consumer settings because of their size, comfort, economy and attenuation characteristics.

Although earplugs may be provided separately, it is often desirable to provide earplugs, or other similar hearing protectors, with suitable attachments to prevent loss should the earplug work itself loose from the wearer's ear or otherwise become dislodged. For example, it is important in the food processing industry to prevent any foreign matter from entering food products. As a result, various types of cords or connectors for attaching a pair of earplugs have been developed, as exemplified in U.S. Pat. No. 5,074,375 to Grozil; U.S. Pat. No. 4,916,758 to Jordan-Ross; U.S. Pat. No. 4,314,553 to Westerdal; U.S. Pat. No. 4,253,452 to Powers et al.; U.S. Pat. No. 4,219,018 to Draper, Jr.; U.S. Pat. No. 4,193,396 to Wacker and U.S. Pat. No. 3,871,372 to Bivins. Typically, the cord is a relatively long, continuous and flexible material fixed to, and extending between, the earplugs or earplug stems. The cord is of sufficient length, generally ranging from between 21 inches to 27 inches, to extend from one ear to the other ear of a wearer while further providing enough slack to secure the cord to some convenient portion of the wearer's apparel, e.g. a shirt collar, or to be draped around the neck of a wearer when not in use. Suitable materials for such cords are conventional in nature and include natural and synthetic materials, for example, cotton, wool, plastic, plastic such as polyvinylchloride, and may be in the form of a continuous solid strand or a braided/twisted multi-strand construction.

While such cords serve their intended function, several disadvantages are associated with their use. For example, at the lengths noted above, the cord itself must be fastened (e.g. using a "cigar-type" band) to prevent tangling and/or knotting during shipping. Therefore, in addition to the extra material needed to fasten the cords, additional handling and preparation for packaging is also required. As such, excessive material waste is of concern as well as maintaining the sanitary integrity of the plugs. Finally, some cords tend to transmit sound through the cord to the earplug, thus reducing the earplugs beneficial intended purpose.

A need therefore remains for alternative attachment mechanisms which provide adequate strength and flexibility to the user.

SUMMARY OF THE INVENTION

Accordingly, the present invention provides an earplug assembly which includes a pair of earplugs adapted for insertion into the ear canal of an individual and an attachment member securely connected to each plug. The attachment member has a first predetermined length and is capable of being extended to a second length. Once extended, the attachment member retains its extended second length.

The present invention provides an alternative attachment mechanism for earplugs which provides users with the ability and flexibility to customize the attachment mechanism to an optimum length and style. In addition, the earplug assembly can be simply and inexpensively produced while minimizing risk of misplacement and loss.

BRIEF DESCRIPTION OF THE DRAWINGS

The foregoing and other objects and advantages of the invention will be appreciated more fully from the following drawings in which.

DETAILED DESCRIPTION OF THE INVENTION

Figure 1:
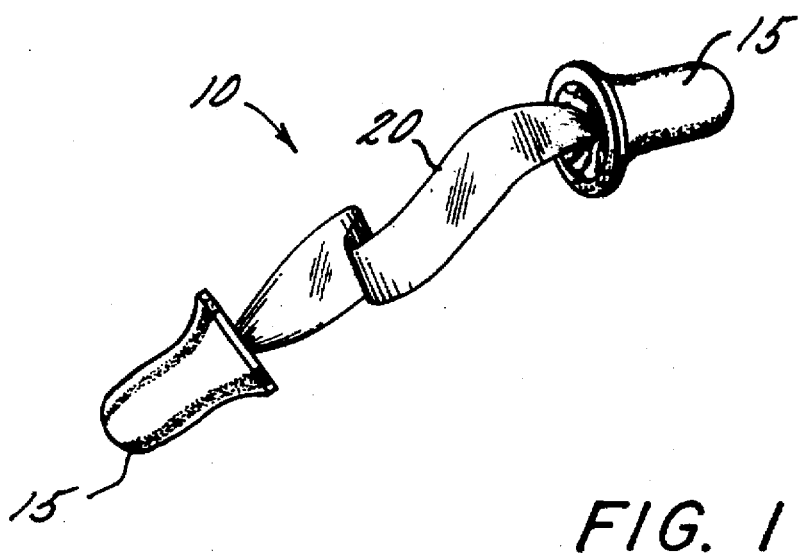
FIG. 1 is a perspective view of an earplug assembly in accordance with the present invention, wherein the attachment member has a first length.
Figure 3:
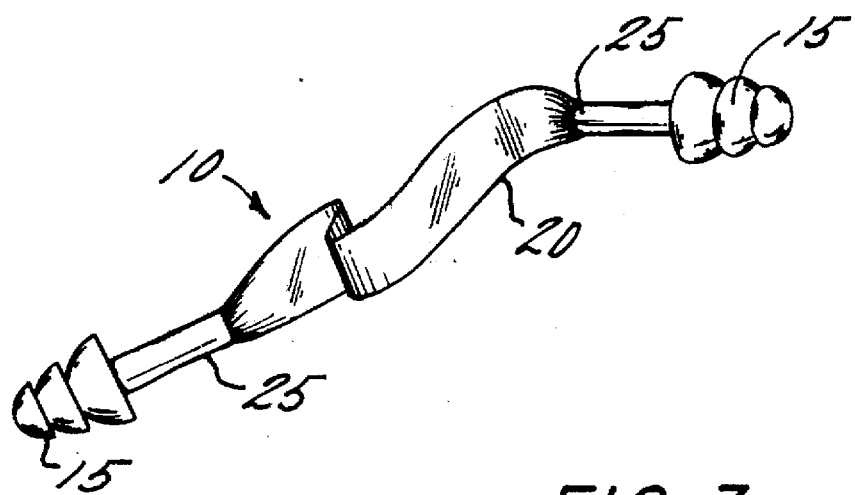
FIG. 3 is a perspective view of a second embodiment of an earplug assembly in accordance with the present invention, wherein the attachment member has a first length affixed to a stem.

Referring to FIGS. 1 and 3, wherein like reference numerals refer to like features, the earplug assembly 10 of the present invention includes a pair of substantially identical earplugs 15 interconnected by an attachment member 20.

Earplugs 15 may be composed of any suitable material, such as polyvinylchloride, polyurethane, silicon rubber and the like. Earplug 15 is shaped for insertion into the ear canal of an individual and will typically be conventional in nature, for example, cylindrical, frusto-conical, bell, single or multiple flanged, pod, bullet-shaped and the like. Furthermore, earplug 15 may include a stem 25 affixed to, or embedded therein, one end thereof.

Figure 2:
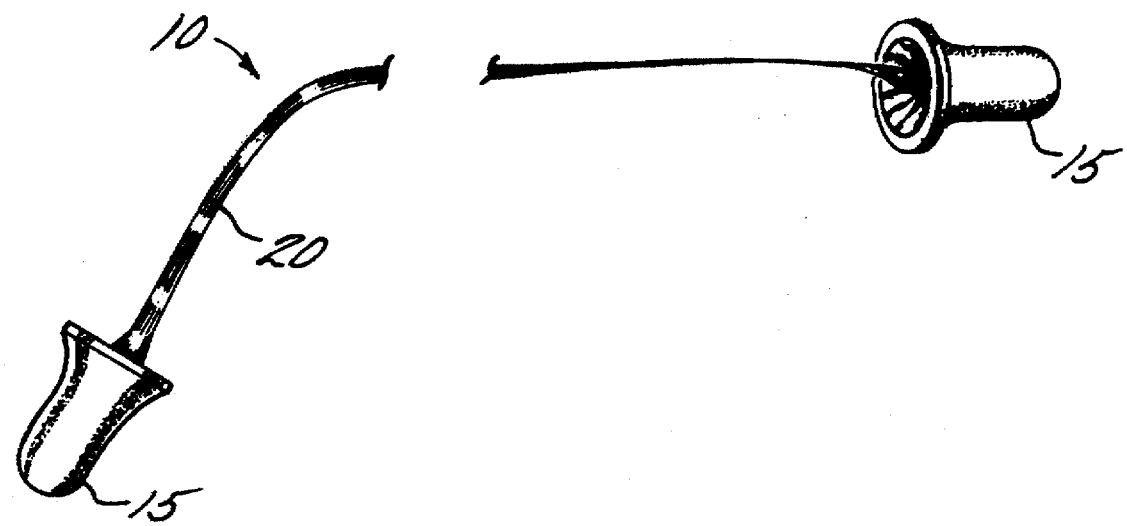
FIG. 2 is a perspective view of the earplug assembly shown in FIG. 1, wherein the attachment member, shown with a broken line, has been extended to a second length.
Figure 4:
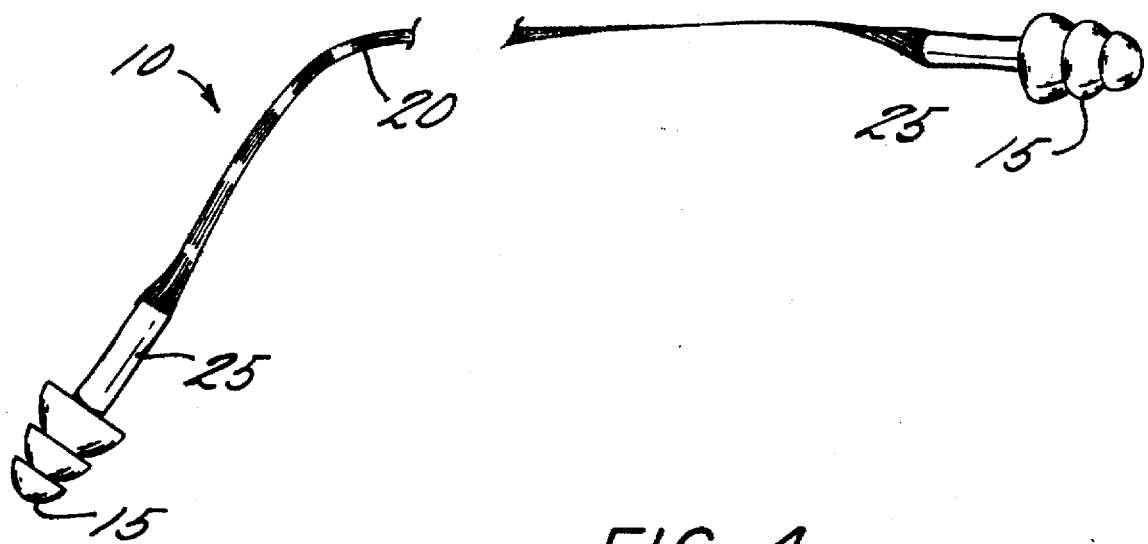
FIG. 4 is a perspective view of the earplug assembly shown in FIG. 3, wherein the attachment member, shown with a broken line, has been extended to a second length.

Attachment member 20 is composed of a flexible material which should be pliant or limp enough to mitigate against transmission of sound to the earplug through the member itself. In addition, the material should be of sufficient strength so as to accomplish its intended purpose of securing earplugs 15 to each other, thereby allowing the wearer to retain the assembly during use or while resting around the wearer's neck. However, the material should not be so strong as to constitute a hazard to the wearer should attachment member 20 become entangled in machinery or other apparatus. In addition, attachment member 20 should possess good tear strength and stretchability properties. Finally, the material of attachment member 20, once extended by the wearer prior to use, must be capable of retaining its extended length, as depicted in FIGS. 2 and 4. In other words, such material should not be of an elastic nature but capable of deformation, i.e. permanent stretch.

In general, materials exhibiting the above properties which have been found to be suitable for use as attachment member 20 include, for example, polypropylene, polyethylene, copolymers of polypropylene and polyethylene, high-impact polystyrene, acrylonitrile-butadiene styrene (ABS) resin and the like. Preferred materials include low density polyethylene (based on octene, hexene, butene & comonomers thereof), ethylene vinyl acetate (EVA), and high density polyethylene. Most preferred are materials which are easily deformed and possess a low modulus, thereby yielding a softer material. Such materials include, for example, linear-low-density polyethylene (LLDPE) and ultra low density ethylene octene copolymers, such as those commercially available as ATTANE® copolymers (ATTANE is a registered trademark of Dow Chemical Company, Midland, Mich.) and as DOWLEX® LLDPE (DOWLEX is a registered trademark of Dow Chemical Company, Midland, Mich.).

The tailoring of the strength and length of attachment member 20 is accomplished by suitable manipulation of the material of construction thereof. By taking into consideration the elongation/stretch factors and other physical properties of the material, a suitable length having a particular cross-sectional dimension may be selected in the shape of a film, cord, tube and the like. Although the first predetermined length of attachment member 20 will vary depending on the material of construction, a length of between 2 inches and 10 inches has been found suitable to provide good strength, flexibility and customization while minimizing excess material during packaging. When the length of attachment member 20 has fallen into the above range, suitable corresponding width and thickness for a film range between ½ and ⅝ inches and 0.002 mils and 0.004 mils, respectively. When the material of construction of attachment member is an ultra low density ethylene octene copolymer, attachment member 20 has a preferred length between 4 inches and 6 inches, width between ½ and ⅝ inches and a dimension thickness between 0.002 mils and 0.004 mils.

Attachment member 20 is securely connected to earplug 15 at its end or, in the alternative, to an earplug stem 25 utilizing conventional techniques, such as mechanical or adhesive bond, thermal-weld, ultrasonic weld and the like. In addition, attachment member 20 may be densifted and inserted into preformed holes.

The second length of attachment member 20 is customized by each wearer to an individual style and comfort by grasping the end of each earplug 15 or earplug stem 25 and slowly pulling the earplugs 15 or stems 25 away from each other in an outwardly direction, thereby elongating or stretching attachment member 20 until the desired length or until a slight resistance is felt. Similar to the first predetermined length, attachment member 20 will have a second length, as illustrated in FIGS. 2 and 4, which will vary from user to user. Typically, it has been found that a second length between about 20 inches and about 30 inches provides sufficient length, security and comfort to the wearer. However, it should be noted that the maximum extended length will be determined by the break resistance of the material of construction.

The present invention provides an earplug assembly having an alternative attachment mechanism which enables users to customize the earplug attachment to an optimum length and personal style. In addition, the earplug assembly is simple and inexpensive to manufacture and minimizes the waste and cost associated with additional fasteners and bulky packaging. For example, it has been found that using the attachment mechanism of the present invention provided a reduction of 80% by weight and 70% in length of the material of construction.

The present invention will be further illustrated by the following examples, which are intended to be illustrative in nature and are not to be construed as limiting the scope of the invention.

EXAMPLE 1

One suitable construction of an earplug assembly 10 in accordance with the present invention was provided by the following combination of elements. The earplug utilized was a three flanged Ultrafit® earplug manufactured by Cabot Safety Corporation, Southbridge, Mass.

| Earplug, 15: | Ultrafit ® Earplug |
|---|---|
| Exposed Stem 25: | ⅝" |
| Attachment Member, 20: | |
| Material | Attane ® Copolymer Film |
| Length | 3½" |
| Width | ½" |
| Thickness | 2 mils |
| Attachment Mechanism | Adhesive (Available from AC-Products) |

The earplug stems were grasped by a user. The user slowly pulled the plugs in an outwardly direction thereby stretching attachment member 20 until the desired second length of 23 inches. Attachment member 20 further has a resulting width of ⅜ inches and a gauge thickness of 0.001 inch.

EXAMPLE 2

In another suitable construction, earplug assembly 10 was provided by the following combination of elements. The earplug utilized was a E.Z.Fit® earplug manufactured by Cabot Safety Corporation, Southbridge, Mass.

| Earplug, 15: | E.Z. Fit ® Earplug |
|---|---|
| Exposed Stem 25: | None |
| Attachment Member, 20: | |
| Material | Attane ® Copolymer Film |
| Length | 4" |
| Width | ⅝" |
| Thickness | 2 mils |
| Attachment Mechanism | thermoweld |

The ends of earplug 15 were grasped by a user. The user slowly pulled the plugs in an outwardly direction thereby stretching attachment member 20 until the desired length of 24 inches. Attachment member 20 further had a resulting width of ⅜ inches and a gauge thickness of 0.001±10% inch.

As illustrated above, the present invention provides an alternative attachment mechanism for earplugs which provides users with the ability and flexibility to customize the attachment mechanism to an optimum length and style without sacrificing strength. In addition, the earplug assembly can be simply and inexpensively produced while minimizing risk of misplacement and loss, as well as the waste associated with additional fasteners.

Although particular embodiments of the invention have been described in detail for purposes of illustration, various modifications may be made without departing from the spirit and scope of the invention. For example, although the present invention has been directed to an earplug assembly, it is believed that the attachment member described herein would be suitable for use on other safety products such as safety prescription and nonprescription eyewear and frames. Attachment member 20 may be suitably affixed to the end of eyewear temples and provide the same advantages as described with respect to earplugs. It should be noted that the material of construction for attachment member 20 would be adjusted accordingly to yield the desired strength and flexibility.

What is claimed is:

1. An earplug assembly comprising:

a pair of earplugs adapted for insertion in the ear canal of an individual; and a single-cord extendable attachment member securely connected between each earplug, wherein said attachment member has a first predetermined length defining a first distance between each earplug, and upon extension to a second length retains its extended second length and defines a second, greater distance between each earplug, and further wherein such extension provides for customization of the second length of the attachment member.

2. The earplug assembly of claim 1 wherein said attachment member comprises a material selected from the group consisting of: polypropylene, polyethylene, copolymers of polypropylene and polyethylene, ABS resin, ethylene vinyl acetate and high impact polystyrene.

3. The earplug assembly of claim 2 wherein said material is a low density polyethylene.

4. The earplug assembly of claim 2 wherein said material is a high density polyethylene.

5. The earplug assembly of claim 2 wherein said material is a linear low density polyethylene.

6. The earplug assembly of claim 2 wherein said material is an ultra low density polyethylene.

7. The earplug assembly of claim 2 wherein said material is an ultra low density polethylene octene copolymer.

8. The earplug assembly of claim 1 wherein said attachment member comprises a material selected from the group consisting of: linear low density polyethylenes based on ethylene, octene, butene, hexene, and copolymers thereof, and ethylene vinyl acetate.

9. The earplug assembly of claim 1 wherein said first predetermined length is between 2 inches and 10 inches.

10. The earplug assembly of claim 9 wherein said first predetermined length is between 4 inches and 6 inches.

11. The earplug assembly of claim 7 wherein said attachment member has a first predetermined length between 2 inches and 10 inches.

12. The earplug assembly of claim 7 wherein said attachment member has a first predetermined length between 4 inches and 6 inches.

13. The earplug assembly of claim 7 wherein said attachment member has a first predetermined width between ½ inches and ⅝ inches.

14. The earplug assembly of claim 7 wherein said attachment member has a thickness between 0.002 inches and 0.004 inches.

15. The earplug assembly of claim 7 wherein said attachment member has a first predetermined length between 4 inches and 6 inches, a width between ½ inches and ⅝ inches, and a thickness between 0.002 inches and 0.004 inches.

16. The earplug assembly of claim 1 wherein said second length is a multiple of said first predetermined length.

* * * * *